United States Patent [19]

Phillipps et al.

[11] Patent Number: 5,003,605

[45] Date of Patent: Mar. 26, 1991

[54] ELECTRONICALLY AUGMENTED STETHOSCOPE WITH TIMING SOUND

[75] Inventors: Patrick G. Phillipps, Lincoln; Paul Epstein, Brookline; David G. Tweed, Chestnut Hill, all of Mass.

[73] Assignee: CardioDyne, Inc., Brookline, Mass.

[21] Appl. No.: 393,781

[22] Filed: Aug. 14, 1989

[51] Int. Cl.⁵ ............................................. A61B 7/04
[52] U.S. Cl. ..................................... 381/67; 128/715
[58] Field of Search ........................... 381/67; 128/715

[56] References Cited

U.S. PATENT DOCUMENTS

| | | | |
|---|---|---|---|
| 3,110,770 | 11/1963 | Howell | 179/1 |
| 3,247,324 | 4/1966 | Cefaly et al. | 179/1 |
| 3,539,724 | 11/1970 | Keesee | 179/1 |
| 3,651,798 | 3/1972 | Egli et al. | 128/2.05 S |
| 3,732,868 | 5/1973 | Willems et al. | 128/2.06 R |
| 3,858,005 | 12/1974 | Marshall et al. | 179/1 ST |
| 3,989,895 | 11/1976 | O'Daniel, Sr. | 179/1 ST |
| 4,048,444 | 12/1977 | Giampapa | 179/1 ST |
| 4,071,694 | 1/1978 | Pfeiffer | 179/1 ST |
| 4,220,160 | 9/1980 | Kimball et al. | 128/715 |
| 4,301,809 | 11/1981 | Pinchak | 128/695 |
| 4,436,096 | 3/1984 | Dyck et al. | 128/689 |
| 4,446,872 | 5/1984 | Marsoner et al. | 128/700 |
| 4,528,690 | 7/1985 | Sedgwick | 381/67 |
| 4,594,731 | 6/1986 | Lewkowicz | 381/67 |
| 4,598,417 | 7/1986 | Deno | 381/67 |
| 4,618,986 | 10/1986 | Hower | 381/67 |
| 4,765,321 | 8/1988 | Mohri | 128/715 |
| 4,770,189 | 9/1988 | Shyu | 128/773 |
| 4,783,813 | 11/1988 | Kempka | 381/67 |
| 4,792,145 | 12/1988 | Eisenberg et al. | 128/715 |
| 4,821,327 | 4/1989 | Furugard et al. | 381/67 |

FOREIGN PATENT DOCUMENTS

| | | |
|---|---|---|
| 0295318 | 12/1988 | European Pat. Off. |
| 2822194 | 4/1980 | Fed. Rep. of Germany |
| 2929688 | 12/1981 | Fed. Rep. of Germany |
| 3218003 | 11/1983 | Fed. Rep. of Germany |
| 2330367 | 11/1975 | France |
| 61-253046 | 10/1986 | Japan |
| 158695 | 6/1979 | Netherlands |

OTHER PUBLICATIONS

Gordon et al., "Electronic Stethoscope with Frequency Shaping & Infransonic Recording Capabilities", Aviation, Space, and Environmental Medicine 312-317 (1976).
Bak, D., "Stethoscope Allows Electronic Amplification", Design News 50-51 (12/15/86).
Abelson, D., "A High-Fidelity Electronic Stethoscope", JAMA 218, 741 (1971).
Allred et al., "Two Electronic Stethoscopes For Use In High Noise Level Environments", 21st Annual Southwestern I.E.E.E. Conference and Exhibition Apr. 1969, San Antonio, TX 6E1-6E6 (1969).
Dowell et al., "Technical Note: Design and Construction of an Electronic Stethoscope", J. of Clinical Engineering 13 355-357 (1988).
Abelson et al., "Bedside Measurement of Systolic and Diastolic Time Intervals Using the Stethometer", Cardiovascular Research, 1977, 11, 270-274.
Patent Reviews, J. Acoust. Soc. Am 79, 888 (1986).
Patent Reviews, J. Acoust. Soc. Am. 81, 584 (1987).

*Primary Examiner*—Forester W. Isen
*Attorney, Agent, or Firm*—Fish & Richardson

[57] ABSTRACT

A stethoscope, operable in an acoustic or electronically augmented mode, is disclosed. In one electronically augmented mode of operation, the stethoscope simultaneously provides the listener with combined unmodified, familiar audible sounds and sounds which have been electronically augmented to bring them within the human auditory range. Additionally, a timing sound may be provided along with the unmodified, familiar audible sounds and electronically augmented sounds to assist the listener in determining when sounds occur in the heart cycle. The timing sound may be enabled in the acoustic mode of stethoscope operation so that the listener can place familiar audible sounds within the heart cycle.

37 Claims, 2 Drawing Sheets

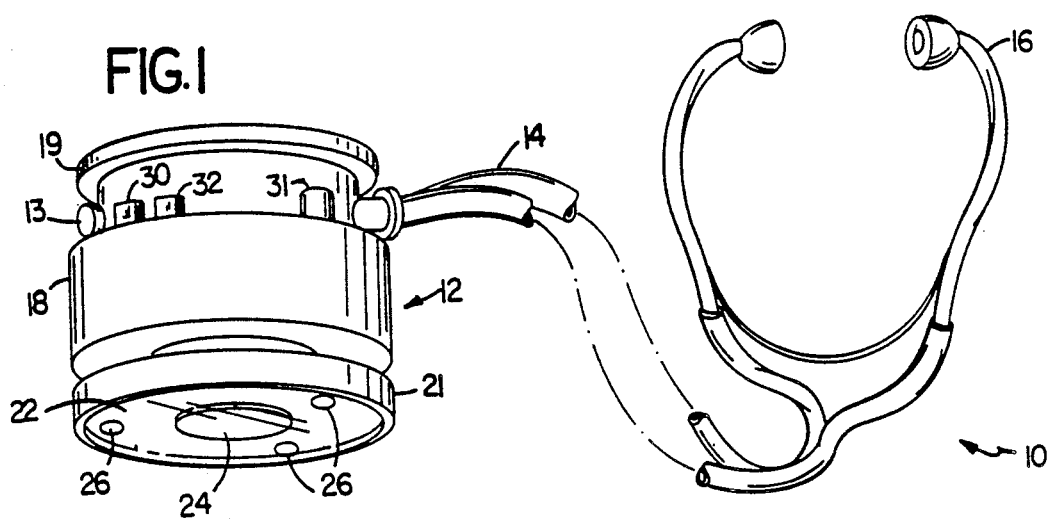
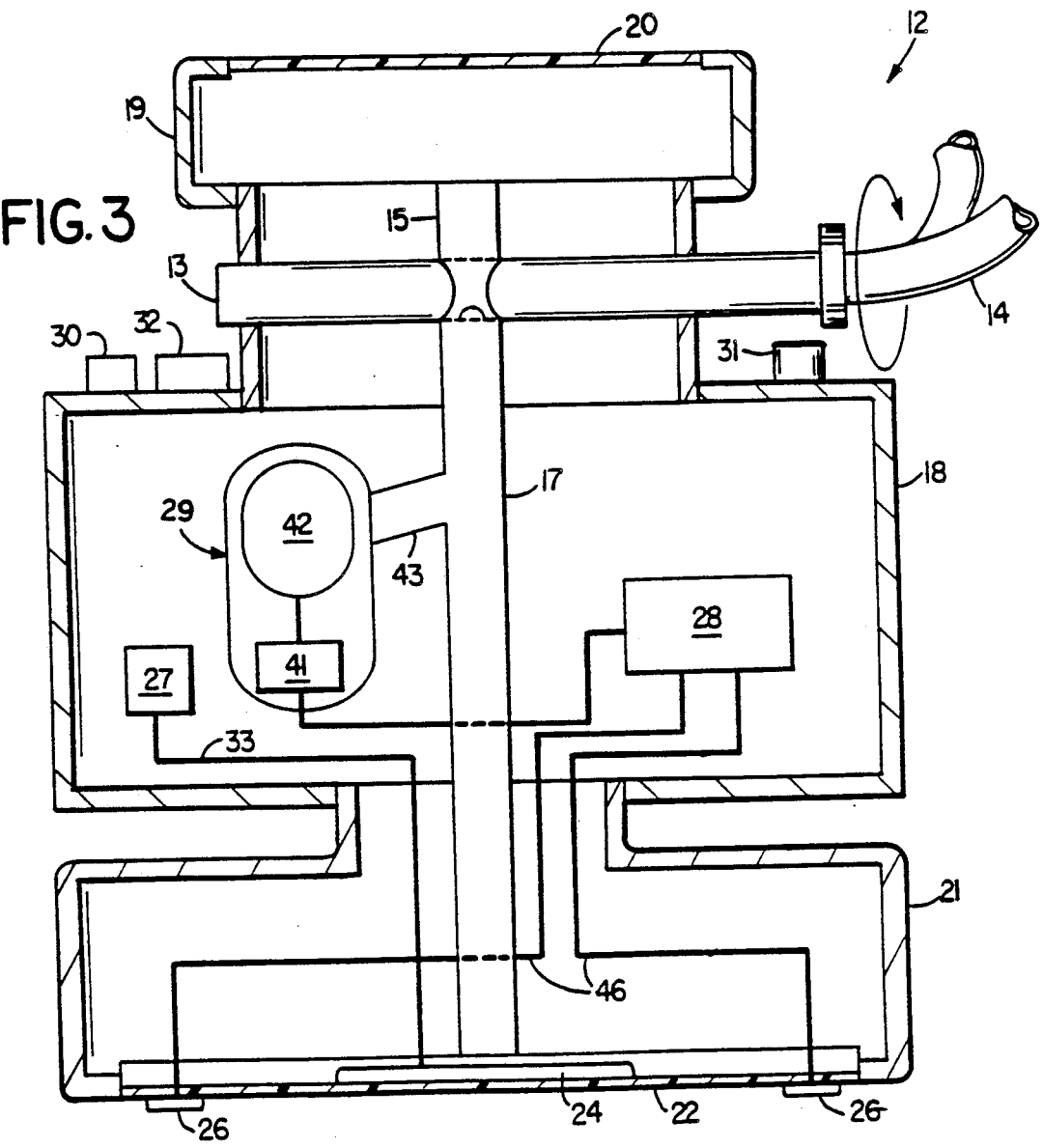

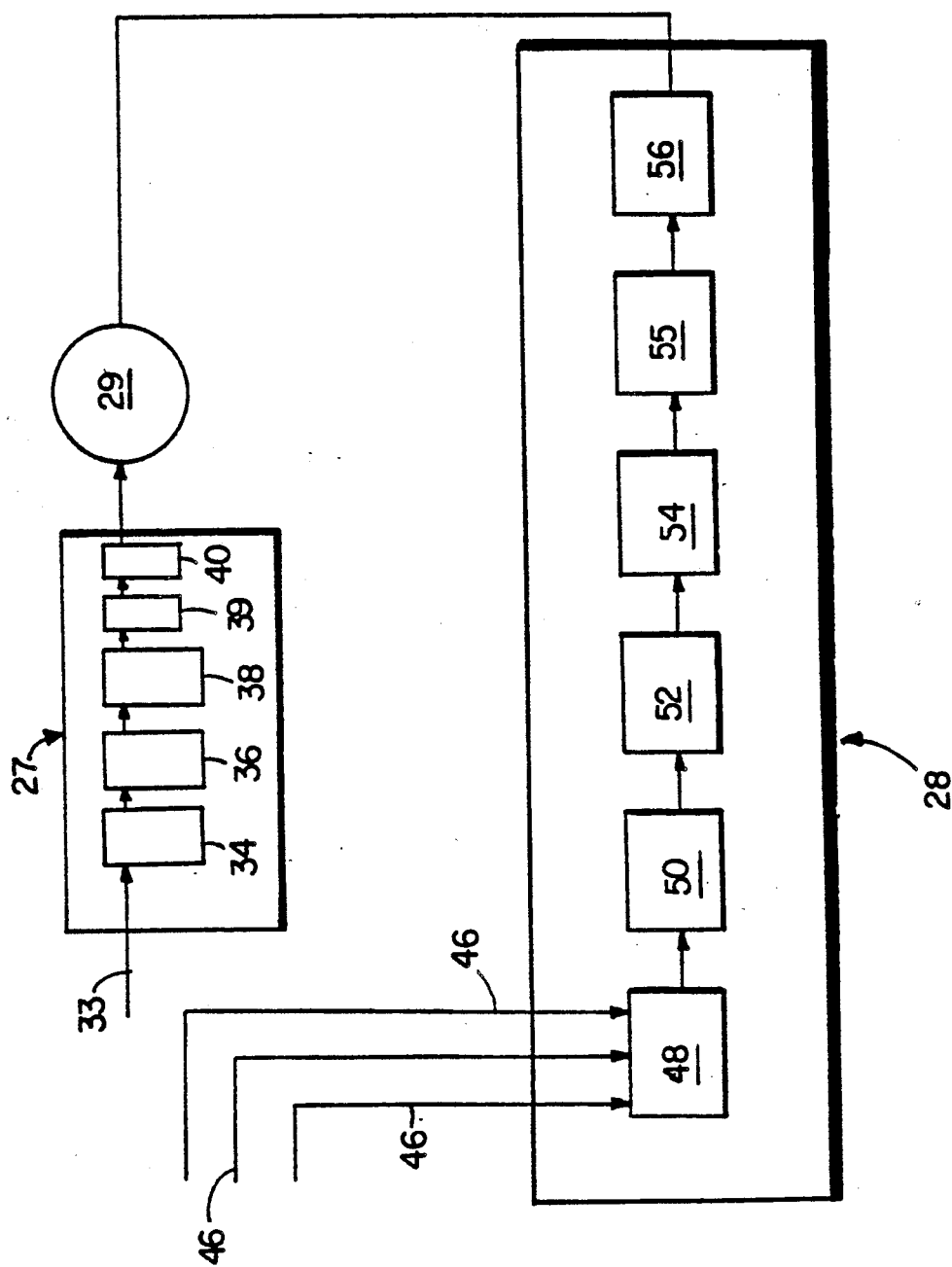

ELECTRONICALLY AUGMENTED STETHOSCOPE WITH TIMING SOUND

BACKGROUND OF THE INVENTION

This invention relates to stethoscopes.

Many of the sounds detected by a stethoscope are faint or fall outside the human auditory range and, therefore, are not effectively perceived by clinicians. Electronic stethoscopes have been developed to make these sounds audible.

SUMMARY OF THE INVENTION

According to one aspect of the invention, a stethoscope provides a listener with access to combined unmodified, high audibility acoustic signals and electronically enhanced signals corresponding to acoustic signals originally outside the human auditory range, when the stethoscope is operated in an augmented mode. These originally inaudible sounds are brought into the human auditory range with an electrical pickup and associated signal processing circuitry which raises the audibility of low frequency signals by optionally multiplying or doubling their frequencies and filters the frequency boosted signals to remove higher order harmonics which are an artifact of the signal processing, and amplifies these signals to optimize audibility.

In another aspect of the invention, a QRS triggered acoustic timing signal generator produces an acoustic timing signal to assist the clinician in determining when particular sounds occur in the heart cycle In preferred embodiments, this acoustic timing signal may be activated with or independently of low audibility signal enhancement. In a preferred embodiment, a pickup for generating electrical signals representative of heart activity for QRS detection and acoustic timing signal triggering are integrated with the stethoscope diaphragm, along with the electrical pickup.

BRIEF DESCRIPTION OF THE DRAWINGS

In the drawings:

FIG. 1 is a somewhat schematic side view of an electronically augmented stethoscope embodying the invention;

FIG. 2 is a block diagram of the electronic circuitry of the stethoscope of FIG. 1;

FIG. 3 is a partially schematic cross section of the bell portion of the stethoscope of FIG. 1.

DESCRIPTION OF THE PREFERRED EMBODIMENT

Referring to FIG. 1, stethoscope 10 consists of bell assembly 12 and rubber tubes 14 for sound transmission to headset 16 Bell assembly 12 integrates electronics module 18, which encloses electronic signal processing circuitry described in detail below. Valve assembly 13 connects with tubes 14 and upper acoustic pathway 15 (FIG. 3). Upper acoustic chamber 19 screws into the top of assembly 13 and module 18 screws into the bottom of assembly 13. Assembly 13 is rotated to allow body sound pickup from either chamber 19 which includes plastic membrane diaphragm 20 or lower bell assembly 21, which contains components for acoustic and electronic sound and electrocardiogram pick-up.

Within the lower bell assembly 21 is plastic membrane diaphragm 22 to which piezoelectric transducer 24 is fastened with an adhesive. Transducer 24 is a polarized polyvinylidene fluoride film sufficiently thin and compliant to insure unimpaired sound response of diaphragm 22 and has approximately one-half the diameter of diaphragm 22. A pattern of three equally spaced semi-circular noble metal deposits sputtered onto diaphragm 22 serves as ECG electrodes 26 for monitoring heart electrical activity.

Referring to FIG. 2, module 18 includes transducer signal processing circuitry 27, ECG and QRS detection circuitry 28, and headset driver 29. On the outside of module 18 (FIG. 1), pushbutton 30 activates transducer circuitry 27, volume control knob 31 adjusts the amplitude of signals emitted by transducer circuitry 27, and slide switch 32 activates QRS detection circuitry 28.

When transducer circuitry 27 is activated, transducer 24 converts vibrations of diaphragm 22 into electrical signals. Referring to FIG. 2, lead 33 transmits these signals to bandpass filter 34. Filter 34, a combination of 4 pole high pass and 2 pole low pass Butterworth response filters having a combined response preferably in the range 16–250 Hz or in a range as wide as 10–500 Hz or as narrow as 30–120 Hz, has its output connected to absolute value circuit 36 for frequency doubling. The frequency doubled signals are filtered by 20 Hz, 2 pole high pass and 200 Hz, 4 pole low pass Butterworth response filters 38 and amplified by low noise amplifier stage 39. Signal amplitude is controlled by potentiometer 40.

Referring to FIG. 3, driver 29 includes power amplifier 41 (approx. 100 mW) and miniature speaker 42, which acts as an electrical-to-audio transducer, to amplify the electrical signals and convert them to acoustic signals. Driver 29 injects these acoustic signals through rubber tube connector 43 into lower acoustic pathway 17 where they merge with acoustic signals coupled conventionally, directly from diaphragm 22.

QRS detection circuitry 28 generates a timing sound for determining when sounds occur in the heart cycle. QRS detection circuitry 28 may be enabled independent of transducer circuitry 27.

Referring to FIG. 2, when QRS detection circuitry 28 is operated, three ECG leads 46 carry signals to low noise high impedance instrumentation amplifier 48 whose output is connected to 2 pole, 25 Hz bandpass filter 50 having Q=1. Adaptive threshold filter 52 recognizes a QRS complex, a narrow, large amplitude signal in the ECG by comparing the peak signal detected to an incoming signal. Pulse generator 54, a one shot monostable multivibrator, produces a timing pulse each time a QRS complex is detected. Lockout delay circuit 55, a monostable multivibrator with a period of approximately 0.25 s, prevents output of spurious timing pulses resulting from noise pickup. Integrated circuit tone generator 56 sends a tone pulse to driver 29, which produces an acoustic timing signal audible to the clinician.

The invention enables a clinician to use a single stethoscope for both conventional acoustic or electronically augmented modes of operation.

In the augmented mode, the stethoscope boosts the amplitude of faint sounds and doubles the frequency of low frequency (16–250 Hz) sounds so that they are brought within the audible range. Such operation is especially useful for detection of inaudible Korotkoff or heart sounds. The acoustic timing signal aids the clinician in identification of heart sounds detected in the acoustic or augmented mode by relating those heart sounds to the electrical activity of the heart and indicating when they occur in the heart cycle. The invention allows the clinician to hear unmodified, familiar audible sounds and electronically augmented sounds simultaneously. The combined virtually identical operation of the stethoscope in the acoustic and augmented modes and availability of familiar medium and high frequency sounds enables effective use of the stethoscope in the augmented mode with little additional clinician training.

What is claimed is:

1. A stethoscope comprising
a first pickup for generating first acoustic signals representative of biological activity in a frequency range that includes frequencies of relatively high audibility,
a second pickup for generating electrical signals representative of biological activity in a frequency range that includes frequencies of relatively low audibility,
an electrical-to-acoustic converter for producing second acoustic signals of enhanced audibility corresponding to said frequencies of relatively low audibility and resembling the sounds of said biological activity in said frequency range of relatively low audibility, and
a transmitter for transmitting to a listener the combination of said first and second acoustic signals.

2. The stethoscope of claim 1 further comprising an amplifier for increasing the intensity of said electrical signals produced by said second pickup.

3. The stethoscope of claim 1 further comprising a first filter for filtering said electrical signals produced by said second pickup to remove said electrical signals representative of biological activity in said frequency range of relatively high audibility.

4. The stethoscope of claim 3 wherein said first filter passes signals in a frequency range between 16 Hz and 250 Hz.

5. The stethoscope of claim 3 wherein said first filter passes signals in a frequency range between 30 Hz and 120 Hz.

6. The stethoscope of claim 3 wherein said first filter passes signals in a frequency range between 10 Hz and 500 Hz.

7. The stethoscope of claim 3 wherein said converter comprises said first filter and a transducer for converting output of said first filter to said second acoustic signals.

8. The stethoscope of claim 7 wherein said converter further comprises a frequency booster for increasing the frequencies of said electrical signals representative of biological activity to enhance their audibility.

9. The stethoscope of claim 8 wherein said frequency booster is a frequency multiplier for multiplying the frequencies of said electrical signals representative of biological activity to enhance their audibility.

10. The stethoscope of claim 9 wherein said frequency multiplier is a frequency doubler for doubling the frequencies of said electrical signals representative of biological activity to enhance their audibility.

11. The stethoscope of claim 8 wherein said converter further comprises a second filter for removing higher order harmonics generated by said frequency booster.

12. The stethoscope of claim 9 wherein said converter further comprises a second filter for removing higher order harmonics generated by said frequency multiplier.

13. The stethoscope of claim 10 wherein said converter further comprises a second filter for removing higher order harmonics generated by said frequency doubler.

14. The stethoscope of claim 8 wherein said converter further comprises an amplifier for amplifying said electrical signals representative of biological activity for enhancing audibility.

15. The stethoscope of claim 14 wherein said converter further comprises a volume control for adjusting the intensity of the amplifier output for optimum audibility.

16. The stethoscope of claim 1 further comprising a frequency booster for increasing the frequencies of said electrical signals representative of biological activity to enhance their audibility.

17. The stethoscope of claim 16 wherein said frequency booster is a frequency multiplier for multiplying the frequencies of said electrical signals representative of biological activity to enhance their audibility.

18. The stethoscope of claim 17 wherein said frequency multiplier is a frequency doubler for doubling the frequencies of said electrical signals representative of biological activity to enhance their audibility.

19. The stethoscope of claim 1 further comprising a branch conduit for transmitting said second acoustic signals to a main conduit wherein said first and second acoustic signals are combined.

20. The stethoscope of claim 1 further comprising a diaphragm for generating said first acoustic signals, and wherein said second pickup for generating electrical signals and a third pickup for generating electrical signals representative of heart activity are attached to said diaphragm.

21. The stethoscope of claim 20 wherein said third pickup comprises three equally spaced metal deposits.

22. The stethoscope of claim 1 further comprising a third pickup for generating electrical signals representative of heart activity.

23. The stethoscope of claim 20, 21, or 22 further comprising a QRS detector for generation of a tone pulse to provide an acoustic timing signal for placing heart sounds within the cardiac cycle.

24. A stethoscope comprising
a pickup for generating first acoustic signals representative of biological activity,
a second pickup for generating electrical signals representative of heart activity during a heart cycle,
an electrical-to-acoustic converter for producing a second acoustic signal in response to said electrical signals representative of heart activity to provide an indication of timing of said heart cycle, and
a transmitter for transmitting to a listener the combination of said first acoustic signals and said second acoustic signal to assist the listener in determining when during said heart cycle said first acoustic signals occur.

25. The stethoscope of claim 24 further comprising a diaphragm for generating acoustic signals, and wherein said second pickup is attached to said diaphragm for generating electrical signals representative of heart activity.

26. The stethoscope of claim 25 wherein said second pickup comprises three equally spaced metal deposits.

27. The stethoscope of claim 24, 25, or 26 further comprising a QRS detector for generation of a tone pulse to activate production of said second acoustic signal by said electrical-to acoustic converter for identifying when heart sounds occur within the cardiac cycle.

28. A stethoscope comprising
- a first pickup for generating first acoustic signals representative of biological activity in a frequency range that includes frequencies of relatively high audibility, said first pickup comprising a diaphragm,
- a second pickup, attached to said diaphragm, for generating electrical signals representative of biological activity in a frequency range that includes frequencies of relatively low audibility,
- a third pickup comprising three equally spaced metal deposits attached to said diaphragm for generating electrical signals representative of heart activity,
- an electrical-to-acoustic converter for producing second acoustic signals of enhanced audibility corresponding to said frequencies of relatively low audibility, and
- a transmitter for transmitting to a listener the combination of said first and second acoustic signals.

29. The stethoscope of claim 28 wherein said electrical-to-acoustic converter also produces a third acoustic signal in response to said electrical signals representative of heart activity, said transmitter transmitting to the listener the combination of said first, second, and third acoustic signals.

30. A stethoscope comprising
- a pickup for generating first acoustic signals representative of biological activity, said pickup comprising a diaphragm,
- a second pickup for generating electrical signals representative of heart activity, said second pickup including three equally spaced metal deposits attached to said diaphragm,
- an electrical-to-acoustic converter for producing a second acoustic signal in response to said electrical signals representative of heart activity, and
- a transmitter for transmitting to a listener the combination of said first acoustic signals and said second acoustic signal.

31. A method for listening to biological activity using a stethoscope, comprising
- generating first acoustic signals representative of biological activity in a frequency range that includes frequencies of relatively high audibility with a first pickup of the stethoscope,
- generating electrical signals representative of biological activity in a frequency range that includes frequencies of relatively low audibility with a second pickup of the stethoscope,
- electrically-to-acoustically converting said electrical signals to second acoustic signals of enhanced audibility that correspond to said frequencies of relatively low audibility and resemble the sounds of said biological activity in said frequency range of relatively low audibility, and
- transmitting to a listener the combination of said first and second acoustic signals.

32. A method for listening to biological activity using a stethoscope, comprising
- generating first acoustic signals representative of biological activity with a pickup of said stethoscope,
- generating electrical signals representative of heart activity during a heart cycle with a second pickup of said stethoscope,
- electrically-to-acoustically converting said electrical signals representative of heart activity to a second acoustic signal to provide an indication of timing of said heart cycle, and
- transmitting to a listener the combination of said first acoustic signals and said second acoustic signal to assist the listener in determining when during said heart cycle said first acoustic signals occur.

33. A stethoscope comprising
- a first pickup for generating first acoustic signals representative of biological activity in a frequency range that includes frequencies of relatively high audibility,
- a second pickup for generating electrical signals representative of biological activity in a frequency range that includes frequencies of relatively low audibility,
- a third pickup for generating electrical signals representative of heart activity,
- an electrical-to-acoustic converter for producing second acoustic signals of enhanced audibility corresponding to said frequencies of relatively low audibility and a third acoustic signal in response to said electrical signals representative of heart activity, and
- a transmitter for transmitting to a listener the combination of said first, second, and third acoustic signals.

34. A stethoscope comprising
- a pair of acoustic pickups each for generating first acoustic signals representative of biological activity in a frequency range that includes frequencies of relatively high audibility, said acoustical pickups being positioned on said stethoscope so that a user can selectively place either of said acoustic pickups adjacent to the body,
- an electrical pickup disposed near a first one of said acoustic pickups for generating electrical signals representative of biological activity in a frequency range that includes frequencies of relatively low audibility when placed with said first acoustical pickup adjacent to the body,
- an electrical-to-acoustic converter for producing second acoustic signals of enhanced audibility corresponding to said frequencies of relatively low audibility, and
- a transmitter for transmitting to the user the combination of said first and second acoustic signals when said first acoustical pickup and said electrical pickup are placed adjacent to the body, and for transmitting only the first acoustic signals to the user when a second one of said pair of acoustical pickups is placed adjacent to the body.

35. The stethoscope of claim 34 further comprising a control device for said electrical-to-acoustic converter that allows the user to selectively activate said electrical-to-acoustic converter.

36. A method for listening to biological activity comprising
providing a stethoscope comprising:
- A. a pair of acoustic pickups each for generating first acoustic signals representative of biological activity in a frequency range that includes frequencies of relatively high audibility,
- B. an electrical pickup disposed near a first one of said acoustic pickups for generating electrical signals representative of biological activity in a frequency range that includes frequencies of relatively low audibility, C. an electrical-to-acoustic converter for producing second acoustic signals of enhanced audibility corresponding to said frequencies of relatively low audibility, and D. a transmitter for transmitting said acoustic signals to the listener, and selectively positioning: said first acoustic pickup and said electrical pickup adjacent to the body to cause said first acoustic signals and said second acoustic signals to be transmitted together to the listener; or said second acoustical pickup adjacent to the body to cause only said first acoustic signals to be transmitted to the listener.

37. The method of claim 36 further comprising enabling the user to selectively activate said electrical-to-acoustic converter.

* * * * *